United States Patent [19]

Zask et al.

[11] Patent Number: 4,997,948
[45] Date of Patent: Mar. 5, 1991

[54] 5-[(1- AND 2-NAPHTHALENYL) SULFONYL]-2,4-THIAZOLIDINEDIONES AND DERIVATIVES THEREOF

[75] Inventors: Arie Zask, Manhattan, N.Y.; Ivo Jirkovsky, Plainsboro, N.J.

[73] Assignee: American Home Products, New York, N.Y.

[21] Appl. No.: 428,817

[22] Filed: Oct. 27, 1989

[51] Int. Cl.$^5$ .......................................... C07D 277/36
[52] U.S. Cl. .................................................. 548/183
[58] Field of Search .......................................... 548/183

[56] References Cited

U.S. PATENT DOCUMENTS

| 4,461,902 | 7/1984 | Kawamatsu et al. | 948/183 |
| 4,687,777 | 8/1987 | Meguro et al. | 514/342 |
| 4,738,972 | 8/1988 | Eggler et al. | 514/314 |
| 4,743,611 | 5/1988 | Malamas et al. | 514/390 |

OTHER PUBLICATIONS

Mohrbachet, R. J. et al., Ann. Rep. Med. Chem. 22, 213-222 (1987).
Yoshioka, T. et al., J. Med. Chem., 32, 421–428 (1989).
Derwent Abst. No. 89:197526t (Japanese Kokai 78 40,770, Publ. 4/13/78).
Derwent Abst. No. 89:179986p (Japanese Kokai 78 46,973, Publ. 4/27/78).
Derwent Abst. No. 74:61927g [Kolomoitsev, L. R. et al., Mikrobiol. Zh. (Kiev), 1970, 32 (4), 518-520 (Ukrain), Copy Attached (AV') (No Translation)].
Fujitu et al., Diabetes, 32, 804-810 (1983).

*Primary Examiner*—Robert Gerstl
*Attorney, Agent, or Firm*—Arthur G. Seifert

[57] ABSTRACT

Disclosed herein are 1- or 2-thio, thiomethylene, and sulfonylnaphthalene derivatives of formulas I and II

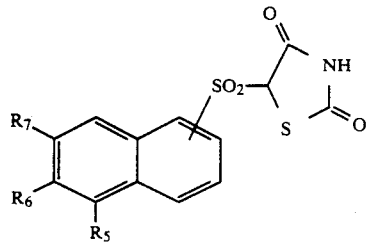

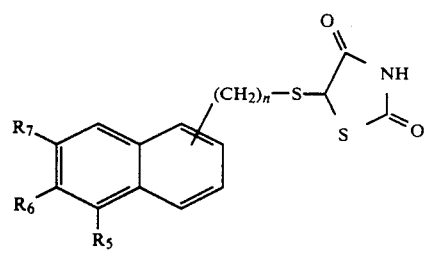

or a pharmaceutically acceptable catonic salt thereof, wherein n is 0 or 1

$R_5$ is hydrogen, bromo, chloro, trifluoromethyl or difluoroethyl;

$R_6$ is hydrogen, hydroxy, methoxy or ethoxy; and $R_7$ is hydrogen or $R_7$ and $R_6$ are both methyl or ethyl carbonate, provided that, when $S(O)_2$ is in the 2 position of the naphthalene ring, $R_5$, $R_6$ and $R_7$ are each hydrogen. The disclosed compounds possess blood-glucose lowering actions and are useful in the treatment of diabetes mellitus.

8 Claims, No Drawings

5-[(1- AND 2-NAPHTHALENYL) SULFONYL]-2,4-THIAZOLIDINEDIONES AND DERIVATIVES THEREOF

The present invention relates to 1- or 1-thio, thiomethylene-, and sulfonylnaphthalene-2,4-thiazolidinedione derivatives of formulas I and II below which posses blood-glucose lowering actions, to processes for their production, to pharmaceutical compositions containing them, and to methods for their use.

BRIEF SUMMARY OF THE INVENTION

This invention provides 1- or 2-sulfonylnaphthalene derivatives of formula

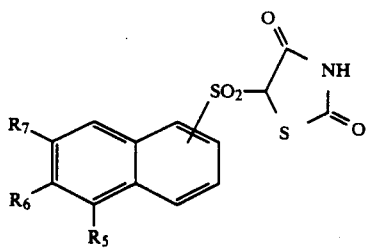

or a pharmaceutically acceptable cationic salt thereof, wherein $R_5$ is hydrogen, bromo, chloro, trifluoromethyl or difluoroethyl;

$R_6$ is hydrogen, hydroxy, methoxy or ethoxy; and $R_7$ is hydrogen or $R_7$ and $R_6$ are both methyl or ethyl carbonate, provided that, when $S(O)_2$ is in the 2 position of the naphthalene ring, $R_5$, $R_6$ and $R_7$ are each hydrogen.

This invention also provides 1- or 2- thio- or thiomethylenenaphthalene derivatives of the formula II

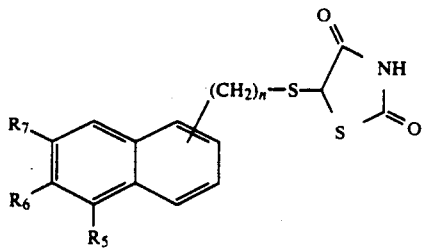

or a pharmaceutically acceptable cationic salt thereof, wherein n is 0 or 1

$R_5$ is hydrogen, bromo, chloro, trifluoromethyl or difluoroethyl;

$R_6$ is hydrogen, hydroxy, methoxy or ethoxy; and $R_7$ is hydrogen or $R_7$ and $R_6$ are both methyl or ethyl carbonate.

The compounds of the invention possess blood glucose lowering actions and are useful in the treatment of diabetes mellitus.

BACKGROUND OF THE INVENTION

Treatment for non-insulin dependent diabetes mellitus (NIDDM; Type II diabetes) usually consists of a regimen of diet and exercise, oral hypoglycemic agents and, in more severe cases, insulin. Oral agents in common use are the sulfonylureas and biguanides. However, while the sulfonylureas are valuable for treatment of NIDDM they may give rise to hypoglycemic episodes and exhibit other toxic manifestations which limit their use. They are also prone to a high incidence of primary or secondary failure of efficacy. Similarly, the use of biguanides has declined because of their association with incidents of toxic lactic acidosis. A continuing need for new hypoglycemic agents which may be less toxic and more efficacious is clearly evident. Pursuit of new oral agents is ongoing and a variety of new and novel compounds with hypoglycemic activity have been reported (Mohrbachet, R. J.; Kiorpes, T. C.; Bowden, C. R. Annular Reports in Medicinal Chemistry—Vol. 22, 1987, pp. 213-222, and references therein).

Ciglitazone [(±)-5-[4-(1-methylcyclohexyl)methoxy]benzyl]-2,4-thiazolidinedione] (U.S. Pat. No. 4,401,902) represents a class of compounds useful for the treatment of hyperglycemia and hyperinsulinemia which only normalize these parameters, thereby avoiding hypoglycemic episodes. Other 2,4-thiazolidinedione containing compounds having antihyperglycemic activity and useful for treating diabetes have been disclosed. See: (a) Yoshioka, T.; Fujita, T.; Kanai, T.; Aizawa, Y.; Kurumada, T.; Hasegawa, K.; Horikoshi, H. J. Med. Chem. 1989, 32, 421, (b) Kanji, M.; Fujita, T. U.S. Pat. No. 4,687,777, 1987, and (c) Eggler, J. F.; Holland, G. F.; Johnson, M. R.; Volkmann, R. A. U.S. Pat. No. 4,738,972, 1988.

The compounds of the present invention also possess antihyperglycemic activity and are of novel structure. They differ from the above compounds by the attachment of a thio or sulfonyl or methylthio linking moiety at the 5-position of the 2,4-thiazolidinedione ring and by the incorporation of a lipophilic naphthalenyl group into the structure. Accordingly, the present compounds represent an important new approach for the treatment of diabetes mellitus.

Compounds in which sulfur is attached to the 5-position of a 2,4-thiazolidinedione ring have been disclosed (Japan Kokai No. 78 40,770; Japan Kokai No. 78 46, 973; Mikrobiol. Zh. (Kiev) 1970, 32, 518-520 (Ukrain); Ger. Offen. DE No. 3,045,059) but differ from the compounds of the present invention in that the nitrogen of the 2,4-thiazolidinedione ring is substituted or the sulfur is in the form of a sulfonic acid. In addition, these compounds are not sulfones and do not contain a naphthalene ring. Furthermore, these compounds are claimed as having only antifouling or antibiotic properties.

The most preferred compounds of formula I are 5-[(2-naphthalenyl)sulfonyl]-2,4-thiazolidinedione and 5-[[6-methoxy-5-(trifluoromethyl)-1-naphthalenyl]sulfonyl]-2,4-thiazolidinedione, and the pharmaceutically acceptable cationic salts thereof.

DETAILED DESCRIPTION OF THE INVENTION

Preferred 1- or 2-sulfonylnaphthalene derivatives of formula I are those in which $R_5$ is hydrogen, bromo or trifluoromethyl. Also preferred are derivatives of formula I in which $R_5$ is trifluoromethyl and $R_6$ is hydrogen or methoxy or those in which $R_5$, $R_6$ and $R_7$ are each hydrogen.

Preferred compounds of formula I are 5-[[6-methoxy-5-(trifluoromethyl)-1-naphthaleneyl]sulfonyl]-2,4-thiazolidinedione; and 5-[(2-naphthalenyl)sulfonyl]-2,4-thiazolidinedione; and the pharmaceutically acceptable cationic salts thereof.

Preferred 1- or 2-thio- or thiomethylenenaphthalene compounds of formula II are those in which $R_5$ is trifluoromethyl and $R_6$ is methoxy or $R_5$, $R_6$ and $R_7$ are each hydrogen. Preferred compounds of formula II are 5-[[(2-naphthalenyl)methyl]thio]-2,4-thiazolidinedione, carbonic acid 6-[(2,4-dioxo-5-thiazolidinyl)thio]-2,3-naphthalenediyl diethyl ester; and 5-[(6-hydroxy-2-naphthalenyl)thio]-2,4-thiazolidinedione, and the pharmaceutically acceptable cationic salts thereof. Most preferred compounds of formula II are 5-[[6-methoxy-5-(trifluoromethyl)-2-naphthalenyl]thio]-2,4-thiazolidinedione and 5-[(2-naphthalenyl)thio-2,4-thiazolidinedione.

The compounds of formulas I and II contain an asymetric center at the 5-carbon of the 2,4-thiazolidinedione ring. The compounds of formula I and II therefore exist, and may be isolated, in one or more racemic and optically active forms. The present invention includes the racemates and the pure enantiomers of the compounds of formulas I and II.

The present invention comprises a method for lowering blood glucose in a hyperglycemic mammal, comprising administering to such mammal an amount of a compound of formula I or II effective to lower blood glucose. The compounds of the present invention may also be used as agents for the treatment of hyperlipidemia and diabetic complications (e.g. neuropathy, nephropathy, ritinopathy, cataracts). Compounds of the present invention, in order to enhance efficacy, may also be used in combination with insulin, sulfonylureas, biguanides, aldose reductase inhibitors and hypolipidemic agents.

The dosage of the compounds of formula I and II of this invention will vary with the particular compound chosen and the form of administration. Furthermore, it will vary with the particular host under treatment. Generally, the compounds of this invention are administered at a concentration level that afford protective effects without any deleterious side effects. For example, the effective amount of compound can usually range from about 10 to about 250 mg/kg body weight per day administered once daily or divided into two to four administrations per week. The optimum dosage for the individual subject being treated will be determined by the person responsible for treatment, generally smaller doses being administered initially and thereafter increments made to determine the most suitable dosage.

Also embraced by the present invention are pharmaceutical compositions, comprising a mixture of a compound by formulas I or II, or a pharmaceutically cationic salt thereof, and a pharmaceutically acceptable carrier, which can be used according to the preceding method.

The novel 2,4-thiazolidinediones of the present invention can be prepared by the processes described hereinafter.

The compounds of formulas I and II form cationic salts with suitable therapeutically acceptable inorganic and organic bases. These derived salts possess the same activity as their parent acid and are included within the scope of this invention. Suitable inorganic bases to form these salts include, for example, the hydroxides, carbonates or bicarbonates of the therapeutically acceptable alkali metals or alkaline earth metals such as sodium, potassium, magnesium, calcium and the like. Suitable organic bases include amines such as benzathine (N,N[1]-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) procaine, etc. Furthermore, there may be mentioned the quarternary salts, for example, the tetralkyl (e.g. tetramethyl), alkyl-alkanol (e.g. methyltriethanol) and cyclic (e.g. N,N-dimethylmorpholine) ammonium salts. In principle, however, there can be used all the ammonium salts which are physiologically compatible.

Transformations to the corresponding salts are readily carried out by reacting the acid form of the compounds of formulas I or II with an appropriate base, usually one equivalent, in a cosolvent. The salt is isolated by concentration to dryness or by adding of a non-solvent. For example, in the case or inorganic salts, it is preferred to dissolve the acid of formula I or II in water containing a hydroxide, carbonate or bicarbonate corresponding to the inorganic salt desired. Evaporation of the solution or addition of a water-miscible solvent of more moderate polarity, for example, a lower alkanol such as butanol, or a lower alkanone such as ethyl methyl ketone, gives the solid inorganic salt. In the case of an amine salt, it is preferred to use a cosolvent of moderate or low polarity such as ethanol, ethylacetate and benzene. Evaporation of the solvent or addition of a miscible diluent of lower polarity such as benzene or n-hexane gives the solid salt. Quaternary ammonium salts may be prepared by mixing the acid of formula I or II with a quarternary ammonium hydroxide in water solution followed by evaporation of the water.

The 2,4-thiazolidinediones of the present invention may be clinically administered to mammals, including man, by either the oral or parenteral route. Oral administration may be either alone or in combination with a solid or liquid pharmaceutically acceptable carrier or diluent such as starch, milk, sugar, certain types of clay, water, vegetable or mineral oils, and so forth to form tablets, capsules, powders, syrups, solutions, suspensions, and the like. For parenteral administration, the active compounds may be used in combination with aqueous or organic media to form injectable solutions or suspensions. For example, solutions in sesame or peanut oil, aqueous propylene glycol and the like may be used as well as aqueous solutions of water and soluble pharmaceutically acceptable salts of the compounds. The injectable solutions prepared in this manner may be administered intraveneously, intraperitoneally, subcutaneously or intramuscularly. The compounds of this invention may also be administered in the form of suppositories.

The db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia. The blood glucose lowering activity of the compounds of formulas I and II of this invention were demonstrated in experiments using such diabetic (db/db) mice, according to the procedure described below.

On the morning of Day 1, 12–15 mice [male db/db (C57BL/KsJ), Jackson Laboratories, 2 to 7 months of age and body weight 35 to 60 gl] were fasted for 4 hours, weighed and a baseline blood sample was collected from the tail-tip of each mouse without anesthesia, placed directly into a fluoride-containing tube, mixed and maintained on ice. Food was then returned to the mice. The plasma was separated and levels of glucose in plasma determined by the Abbott VP Analyzer. Because of the variable plasma glucose levels of the db/db mice, the mice were randomly assigned into 3-5 groups (4-5 mice per group) of equivalent mean plasma glucose levels:

Group A: Vehicle control
Group B: Positive control (ciglitazone)
Group C: 1st Test drug
Group D: 2nd Test drug
Group E: 3rd Test drug On the afternoon of Days 1, 2 and 3 the vehicle, control or test drugs were administered (p.o.) to the ad libitum fed mice. The positive control ciglitazone [(±)-5-[4-[(1-methylcyclohexyl]benzyl]-thiazolidine-2,4-dione] see Fujita et al. Diabetes, 32, 804 (1983), was given by gavage at a dose of 100 mg/kg/day. The test compounds were given by gavage at a dose of 100 mg/kg/day. The fourth and final dose was administered on the morning of day 4, after the mice had been fasted for 18 h. A blood sample was collected immediately preceeding the last dose, followed by samples collected at 90 and 120 min after drug administration. Insulin is immediately administered to each mouse after the 120 min sample. Serial blood samples were collected at 45 and 120 min after insulin administration. The plasma was separated and the levels of glucose in plasma determined by the Abbot VP analyzer.

Analysis of variance followed by Dunnett's multiple comparison (one-sided) was used to estimate the degree of statistical significance of the difference between the vehicle control group and the individual drug-treated groups. A drug was considered active, at the specific dose administered, if the difference of the plasma glucose level has a p<0.10.

The actual difference between the mean percent change of blood glucose levels of the vehicle and the drug-treated group is reported in Table 1. Examination of the results tabulated in Table 1 shows that the compounds of this invention are well suited as antidiabetic agents for they lower blood glucose levels in diabetic (db/db) mice. For example, 5-[(2-naphthalenyl)sulfonyl]-2,4-thiazolidinedione, the compound of Example 4, effects a lowering of blood glucose levels superior to that of ciglitazone at an identical dose of 100 mg/kg.

TABLE 1

| Compound of | Blood Glucose Levels % Change From Vehicle (100 mg/kg) |
| --- | --- |
| Example 1 | −29 |
| Example 2 | −34 |
| Example 3 | −40 |
| Example 4 | −63 |
| Example 5 | −12 |
| Example 6 | −32 |
| Example 7 | −22 |
| Example 11 | −29 |
| Example 13 | −19 |
| Ciglitazone (Positive Control) | −24 to −50 |

The compounds of the present invention are prepared by the processes depicted in Schemes, 1, 2 and 3 below, wherein n, $R_5$, $R_6$, and $R_7$ are as defined below.

Scheme 1

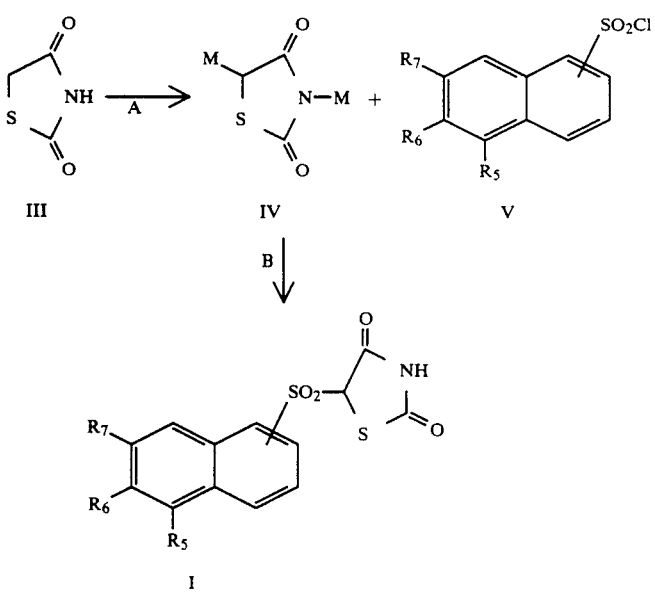

In Scheme 1, the dianion of 2,4-thiazolidinedione IV may be prepared (process A) by treatment of 2,4-thiazolidinedione III with a strong base such as an alkyl- or aryllithium (e.g. n-butyllithium, t-butyllithium, phenyllithium) or an alkali metal amide (e.g. lithium diisopropylamide, potassium bis-(trimethylsilyl(amide). The reaction may be carried out in an ether type solvent such as tetrahydrofuran under the atmosphere of nitrogen or other inert gas at a temperature between −90° C. and 40° C. A preferred method of preparation of the dianion IV is by addition of the base over a period of 1-10 min to a solution of 2,4-thiazolidinedione in tetrahydrofuran maintained at about −78° C. After 5-30 min the reaction mixture is warmed to 0° C. for 15-45 min. Once dianion formation is complete the mixture may be stored at −78° C. for several hours. Another method for the preparation of the dianion of 2,4-thiazolidinedione has been reported (J. D. Taylor and J. F. Wolfe Synthesis, 1971, 310). This method requires the use of lithium or potassium amide in liquid ammonia.

The reaction of the dianion of formula IV with arylsulfonyl chlorides of formula V (process B) gives the corresponding 5-arylsulfonyl-2,4-thiazolidinediones I.

The arylsulfonyl chloride may be added to the dianion mixture (prepared as described above) as a solution in an ether type solvent such as tetrahydrofuran, or as a solid. During the course of the addition, the dianion mixture is maintained at about −78° C. The time for the addition may range from 10 sec to 30 min. After the addition, the resulting reaction mixture is maintained at about −78° C. for 5 min to 60 min, then allowed to warm to about 25° C. After 1–4 h the reaction mixture is acidified with solid ammonium chloride and then a strong protic acid such as aqueous sulfuric acid. The product may then be isolated by methods well known in the art. Advantage may be taken of the acidity of these compounds to separate them from non-acidic organic impurities by their dissolution in an aqueous base solution of sodium bicarbonate or similar base. Further purification may be accomplished by well known methods such as chromatography and recrystallization.

Scheme 2

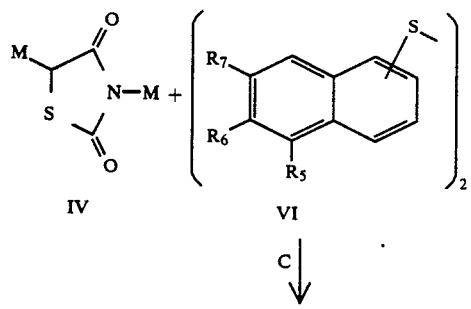

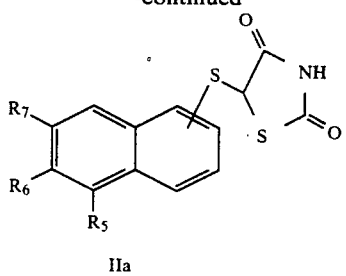

IIa

In Scheme 2, reaction of the dianion IV with an appropriate aryl disulfide VI (process C) gives the corresponding 5arylthio-2,4-thiazolidinedione 11a. The disulfide may be added to the dianion as a solution in an ether type solvent such as tetrahydrofuran. The dianion mixture (prepared as described above) may be maintained at a temperature between −78° C. and 40° C. during the course of the addition. A preferred temperature is about 25° C. A preferred addition time is 1–15 min. After the addition is complete, the resulting mixture is maintained at 25° C. for 1–4 h. It is then acidified with a strong protic acid such as aqueous hydrochloric acid. The crude product may be isolated by methods well known in the art. Further purification may be accomplished by well known methods such as chromatography and recrystallization. Disulfides may be prepared by known methods such as the reductive coupling of sulfonyl chlorides by hydriodic acid according to the procedure of W. A. Slippared Org. Syn. Coll., Vol. 5, 1973, 843.

Scheme 3

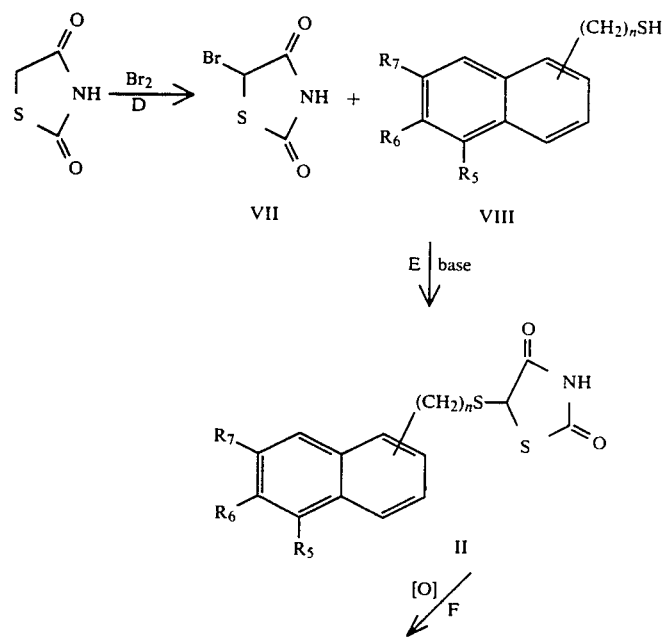

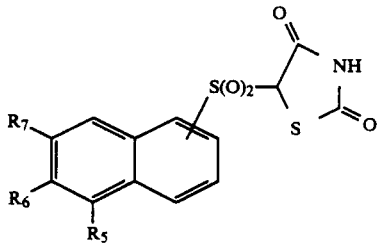

In Scheme 3, an alternate method of preparing 5-arylthio- and 5-aralkylthio-2,4-thiazolidinediones of formula II, by reaction of an appropriate mercaptan with 5-bromo-2,4-thiazolidinedione VII and a suitable base in an ether type solvent, such as tetrahydrofuran, is shown (process E). A preferred procedure is to treat a solution of a mercaptan of formula VIII and 5-bromo-2,4-thiazolidinedione VII in tetrahydrofuran at about −78° C. under a nitrogen atmosphere with two or more equivalents of lithium diisopropylamide or lithium bis(-trimethylsilylamide). After the addition of base is complete, the mixture is held at about −78° C. for 10–60 min, then warned to about 25° C. After 30–120 min the mixture is acidified with an acid such as aqueous hydrochloric acid. The product may be isolated and purified by methods well known in the art.

The 5-bromo-2,4-thiazolidinedione of formula VII may be prepared (process D) by treatment of a solution of 2,4-thiazolidinedione III with bromine in an appropriate solvent. A preferred procedure involves treatment of a solution of 2,4-thiazolidinedione in acetic acid with one equivalent of bromine at about 85° C. for 1–3 h.

The sulfides of formula II may be converted to the corresponding sulfones of formula I (process F) by treatment with a suitable oxidizing agent. A preferred method for the preparation of sulfones is by treatment with an excess of hydrogen peroxide in acetic acid at 50° C.

The sulfonyl chlorides of formula V are commercially available compounds or may be prepared by known methods. For example, by the regioselective chlorosulfonylation of an appropriate substituted naphthalene. The sulfonyl chlorides of formula V may also be prepared from the corresponding sulfonic acid or sodium sulfonates by treatment with phosphorus pentachloride or similar reagent. Preparation of 5-methoxy-5-(trifluoromethyl)-1-naphthalenesulfonyl chloride may be accomplished as described by M. S. Malamas and K. Sestanj, U.S. Pat. No. 4,743,611. Carbonic acid 6-sulfonylchloro-2-naphthalenyl ethyl ester and carbonic acid 6-sulfonylchloro-2,3-naphthalendiyl diethyl ester were prepared as described by T. Zincke and R. Dereser Chem. Ber. 1917, 51, 352.

The mercaptans of formula VIII are commercially available or may be prepared by known methods. They may be conveniently prepared from the corresponding sulfonyl chlorides by a reduction, such as with zinc/hydrochloric acid. Synthesis of 2-(mercaptomethyl)naphthalene may be carried out according to the procedure of G. G. Urquhart, J. W. Gates, and R. Conner Org. Syn. Coll. Vol. 3, 363, starting from 2-(bromomethyl)-naphthalene and thiourea. Carbonic acid 6-mercapto-2-naphthalenyl ethyl ester and carbonic acid 6-mercapto-2,3-naphthalendiyl diethyl ester were prepared as described by T. Zincke and R. Dereser Chem. Ber., 1917, 51, 352.

Preparation of 5-[(6-hydroxy-2-naphthalenyl)thio]-2,4-thiazolidinedione from carbonic acid 6-[(2,4-dioxo-5-thiazolidinyl)thio]-2-naphthalenyl ethyl ester may be done by a saponification reaction with a suitable base. A preferred method involves treatment of a suspension of the carbonic acid ethyl ester in methanol with potassium hydroxide at about 25° C. for 15–45 min.

The following examples further illustrate this invention.

EXAMPLE 1

5-[(5-Bromo-1-naphthalenyl)sulfonyl]-2,4-thiazolidinedione

To a solution of 2,4-thiazolidinedione (5.5 g, 47.2 mmol) in tetrahydrofuran (275 mL) at −78° C. was added n-butyllithium (62 mL, 99 mmol, 1.6M in hexanes). After 1.5 hr at −78° C., 5-bromo-1-naphthalenesulfonyl chloride (15.9 g, 52 mmol) was added as a solid, all at once. After 30 min at −78° C., the orange solution was allowed to arm to 25° C. After 1.5 h excess solid ammonium chloride was added and the mixture partitioned between 5% aqueous sulfuric acid and chloroform. The aqueous phase was washed an additional two times and the combined chloroform extracts were dried (magnesium sulfate) and concentrated to give a brown oil. The oil was partitioned between 5% aqueous sodium bicarbonate and chloroform. The aqueous phase was washed with chloroform (233 ) then acidified to pH 1 with conc. hydrochloric acid and extracted with chloroform (3×). The combined organic extracts were dried (magnesium sulfate) and concentrated. Flash chromatography (110 g silica gel pretreated with 2% H3PO4/MeOH; CHCl3:CH3CN, 10:1) gave the product as a foam (7.6 g, 42% yield). Crystallization from chloroform gave a powder (5.8 g) which was recrystallized from acetonitrile/chloroform to give the analytically pure product as large irregular crystals (1.5 g). m.p. 189°–190° C.

IR (KBr): 3435 (bd), 3200 (bd), 1766 (m), 1752 (m), 1687 (s), 1333 (s), 1158 (m), 1133 (m), 789 (m) cm$^{-1}$.

MS (DCI) m/e (rel. intensity): 386 (M+H, 2), 271 (NpSO$_2$, 16), 269 (NpSO$_2$, 18), 207 Np, 60), 205 (Np, 54), 126 (58) 99 (50).

$^1$H NMR (DMSO-d$_6$, 200 MHz): δ6.60 (s, 1H, —CH—, exchanges with D$_2$O), 7.71 (dd, J=7.3, 8.7 HZ, 1H, NpH), 7.94 (dd, J=7.3, 8.4 Hz, 1H, NpH), 8.14 (d, J=7.3 Hz, 1H, NpH), 8.35 (d, J=7.6 Hz, 1H, NpH), 8.68 (d, J=8.9 HZ, 2H, NpH).

Analysis Calculated: C, 40.42; H, 2.09; N, 3.63. Found: C, 40.58; H, 2.13; N, 3.84.

Examples 2 and 3

The compounds of Examples 2 and 3 were prepared by the procedure described in Example 1 from the dianion of 2,4-thiazolidinedione and the appropriate sulfonyl chloride V.

EXAMPLE 2

5-[(1-Naphthalenyl)sulfonyl]-2,4-thiazolidinedione m.p. 187°–188° C.

IR (KBr): 3430 (bd), 3200 (bd), 1778 (m), 1700 (s), 1327 (s), 1160 (m), 1129 (s), 764 (m) cm$^{-1}$.

$^1$H NMR (DMSO-d$_6$, 400 MHz): δ6.57 (s, 1H, —CH—), 7.71–7.85 (m, 3H, NpH), 8.20 (d, J=8.1 Hz, 1H, NpH), 8.24 (d, J=7.4 Hz, 1H, NpH), 8.45 (d, J=8.2 Hz, 1H, NpH) 8.60 (d, J=8.6 Hz, 1H, NpH).

Analysis Calculated: C, 50.80; H, 2.96; N, 4.56. Found: C, 51.05; H, 3.16; N, 4.56.

EXAMPLE 3

5-[[(6-Methoxy-5-(trifluoromethyl)-1-naphthalenyl]-sulfonyl]-2,4-thiazolidinedione m.p. 211°–212° C.

IR (KBr): 3217 (bd), 1778 (m), 1708 (s), 1510 (s), 1323 (s), 1126 (s), 1009 (m), 818 (m) cm$^{-1}$.

MS (El) m/e (rel. intensity): 405 (M$^{30}$, 12.5) 289 (NpSO$_2$, 61), 225 (Np, 92) 195 (23), 182 (34), 177 (100), 175 (23), 151 (17).

$^1$H NMR (DMSO-d$_6$, 400 MHz): δ4.11 (s, 3H, —OCH$_3$), 6.34 (s, 1H, —CH—), 7.85 (d, J=9 Hz, 1H, NpH), 7.90 (dd, J=7.5, 6.6 Hz, NpH), 8.25 (d, J=7.4 Hz, 1H, NpH), 8.59 (d, J=8.1 Hz, 1H, NpH), 9.06 (d, J=9.7 Hz, 1H, NpH).

Analysis Calculated: C, 44.44; H, 2.49; N, 3.45. Found: C, 44.44, H, 2.45; N, 3.43.

EXAMPLE 4

5-[(2-Naphthalenyl)sulfonyl]-2,4-thiazolidinedione

5-[(2-Naphthalenyl(thio)-2,4-thiazolidinedione (2.50 g, 9.08 mmol) was dissolved in acetic acid (100 mL) and heated to 60° C. whereupon 30% aqueous hydrogen peroxide (30 mL, 264 mmol) was added. After 3 h in the hot mixture was poured into water (600 mL). The aqueous phase was extracted with ethyl acetate (3×). The combined ethyl acetate extracts were dried over magnesium sulfate, filtered, and concentrated to give an oil. The oil was chromatographed trouch C-18 silica gel (70:30 methanol:water) to give a pink foam (1.74 g). The foam crystallized from hexane:chloroform:methanol to give white needles (1.308 g, 46.9% yield). m.p. 196°–197° C.

$^1$H NMR (DMSO-d$_6$, 400 MHz) δ6.75 (s, 1H, SCH), 7.72–7.83 (m, 2H, ArH), 7.91 (dd, J=8.2 Hz, 1H, ArH), 8.12 (d, J=8 Hz, 1H, ArH), 8.23 (d, J=8 Hz, 1H, ArH), 8.26 (d, J=8 Hz, 1H, ArH), 8.64 (d, J=2 Hz, 1H, ArH)

MS (El) m/e (rel. intensity) 307 (M$^{30}$, 12).

Analysis Calculated: C, 50.80; H, 2.95; N, 4.56. Found: C, 50.84; H, 3.32; N, 4.53.

EXAMPLE 5

5-[[(2-Naphthalenyl)methyl]thiol]-2,4-thiazolidinedione

Lithium diisopropylamide (29 mL, 56.1 mmol, 1.94M in tetrahydrofuran) was added to a solution of 5-bromo-2,4-thiazolidinedione (5.0 g, 25.2 mmol) and 2-(mercaptomethyl)naphthalene (4.45 g, 25.5 mmol) in tetrahydrofuran (200 mL) at −78° C. under nitrogen atmosphere. After 30 min the reaction mixture as allowed to warm to 25° C. and after an additional 90 min the mixture was treated with aqueous hydrochloric acid (2.0N). The resulting aqueous mixture was extracted with ethyl acetate (3×). The combined ethyl acetate extracts were dried over magnesium sulfate, filtered, and evaporated to give an oil (7.28 g). The oil was crystallized from chloroform:ethyl acetate to give off-white needles (4.13 g, 56.0% yield). m.p. 173°–174° C.

$^1$H NMR (DMSO-d$_6$, 400 MHz) δ4.15 (d, J=13 Hz, 1H, SCH$_2$), 4.19 (d, J=13 Hz, 1H, SCH$_2$), 5.67 (s, 1H, —SCH), 7.44–7.54 (m, 3H, ArH), 7.83 (s, 1H, ArH), 7.85–7.92 (m, 3H, ArH)

IR (KBr): 3410 (bd, NH), 1702 (s, C=0), 1324 (s), 1170 (s), 818 (s), 620 (m) cm$^{-1}$.

MS (El) m/e (rel. intensity): 289 (M+, 13).

Analysis Calculated: C, 58.11; H, 383; N, 4.84. Found: C, 58.02; H, 3.91; N, 4.79.

Examples 6, 7 and 8

The compounds of Examples 6, 7 and 8 were prepared by the procedure described in Example 5 from the 5-bromo-2,4-thiazolidinedione VII and the appropriate mercaptan VIII.

EXAMPLE 6

5-[[6-Methoxy-5-(trifluoromethyl)-2-naphthalenyl]thiol-2,4-thiazolidinedione

Prepared in 34% yield.

m.p. 153°–154° C.

$^1$H NMR (DMSO-d$_6$, 400 MHz) δ4.02 (s, 3H, —OCH$_3$), 6.17 (s, 1H, —CH—), 7.67–7.72 (m, 2H, ArH), 8.05 (d, J=9.1 Mz, 1H, ArH), 8.23 (s, 1H, ArH), 8.30 (d, J=9.3 Hz, 1H, ArH).

EXAMPLE 7

Carbonic acid 6-[2,4-dioxo-5-thiazolidinyl)thio]-2,3-naphthalenediyl diethyl ester Prepared in 54% yield.

m.p. 138°–139° C.

$^1$H NMR (DMSO-d$_6$, 400 MHz) δ1.30 (t, J=7.0 Hz, 6H, —CH$_3$), 4.29 (q, J=7.0 Hz, 4H, —CH$_2$—), 6.22 (s, 1H, —CH—), 7.66 (d, J=8.5 Hz, 1H, ArH), 8.00 (d, J=8.6 Hz, 1H, ArH), 8.04 (s, 1H, ArH), 8.05 (s, 1H, ArH), 8.18 (s, 1H, ArH).

EXAMPLE 8

Carbonic Acid 6-[(2,4-dioxo-5-thiazolidinyl)thio]-2-naphthalenyl ethyl ester m.p. 127°–128° C.

$^1$H NMR (DMSO-$_6$, 400 MHz) δ1.31 (t, J=8 Hz, 3H, —CH$_3$), 4.28 (q, J=8 Hz, 2H, —OCH2—), 6.19 (s, 1H, —SCH—), 7.49 (dd, J=8, 4Hz, 1H, ArH), 7.63 (dd, J=8, 4 Hz, 1H, ArH), 7.83 (d, J=2 Hz, 1H, ArH), 7.96 (d, J=8Hz, 1H, ArH), 8.04 (d, J=8 Hz, 1H, ArH), 8.18 (s, 1H, ArH).

IR (KBr): 3425 (bd, NH), 1741 (s), 1698 (s, C=O), 1282 (s), 1200 (m), 999 (w) cm$^{-1}$.

MS (El) m/e (rel. intensity): 363 (M+, 10), 291 (8), 175 (100), 131 (74), 102 (38).

Analysis Calculated: C, 52.88; 3.60; N, 3.85. Found: C, 52.83; H, 3.70; N, 3.85.

EXAMPLE 9

2-(Mercaptomethyl)naphthalene

Utilizing the procedure of G. G. Urquhart, J. W. Gates and R. Conner, Org. Syn. Coll. Vol. 3, p. 363, thiourea (6.89 g, 90.5 mmol) was added to a solution of 2-(bromomethyl)naphthalene (20.6 g, 90.5 mmol) in anhydrous ethanol (100 mL) and then heated at reflux. After 17 h, the reaction solution was concentrated to an oil. The oil was dissolved in a solution of potassium hydroxide (11.2 g, 199 mmol) in water (100 mL) and heated at reflux for 2 h. The solution was then cooled to 25° C. and treated with aqueous hydrochloric acid (2.0N). The resulting aqueous mixture was extracted with ethyl acetate (3×). The combined ethyl acetate extracts were dried over magnesium sulfate, filtered and evaporated to give yellow crystals (14.5 g, 91.9% yield).

$^1$H NMR (acetone-d$_6$, 200 MHz) δ2.25 (t, J=6 Hz, 1H, -SH), 3.94 (d, J=6 Hz, 2H, —CH2—), 7.40–7.60 (m, 3H, ArH), 7.80–8.00 (m, 4H, ArH).

EXAMPLE 10

5-Bromo-2,4-thiazolidinedione

To a solution of 2,4-thiazolidinedione (100 g, 0.855 mol) in acetic acid (250 mL) at 85° C. was added bromine (42.68 mL, 0.855 mol) dropwise over a period of 1 h. After an additional 1 hr at 85° C. the reaction solution was allowed to cool to 25° C., then poured into water (1L). The aqueous phase was extracted with ether (3×). The combined ether extracts were dried over magnesium sulfate, filtered and concentrated. The resulting yellow oil (127 g) was filtered through a plug of silica eluting with chloroform:acetonitrile (8:1). A colorless oil was obtained which was triturated with hexane to give a white powder (95.0 g, 56.7% yield).

m.p. 61°–62° C.

$^1$H NMR (Acetone-d$_6$, 200 MHz) δ6.41 (s, 1H, —CH—), 11.30 (s, 1H, —NH) IR (KBr): 3250 (bd, NH), 1774 (s, doublet), 1710 (s, C=O), 1305 (s), 1142 (s), 812 (m), 728 (m), 700 (m) cm$^{-1}$.

MS (EI) m/e (rel. intensity): 197 (M+, 49), 195 (M+, 48), 154 (42), 152 (41), 126 (36), 116 (100).

Analysis Calculated: C, 18.38; H, 1.02; N, 7.15. Found: C, 18.81; H, 0.46; N, 7.39.

EXAMPLE 11

5-[(2-Naphthalenyl)thio]-2,4-thiazolidinedione

Lithium diisopropylamide (40.26 mL, 78.1 mmol, 1.94M in tetrahydrofuran) was added to a solution of 2,4-thiazolidinedione (5.15 g, 35.5 mmol) in tetrahydrofuran (150 mL) at −78° C. under a nitrogen atmosphere. The resulting floculant suspension was allowed to warm to 25° C. whereupon a solution of 2-naphthalenedisulfide (11.32 g, 35. 5 mmol) in tetrahydrofuran (250 mL) was added as a slow stream through a cannula. After 2 h the reaction solution was treated with 2.0N hydrochloric acid (200 mL) and the resulting aqueous suspension was extracted with ethyl acetate (3×). The combined ethyl acetate extracts were dried over magnesium sulfate, filtered, and concentrated to give a yellow solid (16.19 g). The yellow solid was chromatographed through silica gel (pretreated with 2% phosphoric acid in methanol) eluting with chloroform to give off-white crystals (2.39 g, 24.5% yield). Recrystallization from hot chloroform gave analytically pure crystals (1.19 g).

m.p. 137°–138° C. $^1$H NMR (DMSO-d$_6$, 400 MHz) δ6.20 (s, 1H, —SCH—), 7.56–7.61 (m, 3H, ArH), 7.94–7.97 (m, 3H, ArH), 8.13 (d, J=2 Hz, 1H, ArH).

IR (KBr): 3300 bd, NH), 1748 (s), 1679 (s, C=O), 1310 (m), 827 (m) cm$^{-1}$.

MS (EI) m/e (rel. intensity): 275 (M$^{30}$, 29), 159 (92), 115 (100).

Analysis Calculated: C, 56.71; H, 3.29; N, 5.09. Found: C, 56.19, H, 3.40; N, 5.15.

EXAMPLE 12

2-Naphthalenedisulfide

Utilizing the procedure of W. A. Sheppard Org. Syn. Coll. Vol. 5, 843 2-naphthalenesulfonyl chloride (20 g, 88.2 mmol) was dissolved in aqueous concentrated hydriodic acid (100 mL, 368 mmol) and heated at reflux for 4 h. The resulting solution was allowed to cool to 25° C. and then poured into water (500 mL). The aqueous suspension was neutralized to pH=7.0 by addition of solid sodium bicarbonate, treated with solid sodium bisulfate, and then extracted with chloroform (3×). The combined chloroform extracts were dried over magnesium sulfate, filtered, and concentrated to give an off-white solid (13.2 g, 94.0% yield).

$^1$H NMR (CDCl$_3$, 200 MHz) δ7.40–7.50 (m, 2H, ArH), 7.61 (d, J=2Hz, 1H, ArH), 7.66 (d, J=2 Hz, 1H, ArH), 7.69–7.92 (m, 2H, ArH), 7.98 (d, J=2 Hz, 1H, ArH).

EXAMPLE 13

5-[(6-Hydroxy-2-naphthalenyl)thio]-2,4-thiazolidinedione

Potassium hydroxide (2.47 g, 44.0 mmol) was added to a stirred suspension of carbonic acid 6-[(2,4-dioxo-5-thiazolidinyl)thio]-2-naphthalenyl ethyl ester (8.0 g, 22.0 mmol) in methanol (50 mL) at 25° C. After 30 min the resulting homogeneous solution was acidified with aqueous hydrochloric acid (2.0N), concentrated to remove methanol, and then extracted with ethyl acetate (3×). The combined ethyl acetate extracts were dried over magnesium sulfate, filtered, and evaporated to give a yellow powder (6.40 g, 99.8% yield). The powder crystallized from hot chloroform:ethyl acetate to give the analytical sample as off-white crystals. m.p. 182°–183° C.

$^1$H NMR (DMSO-d$_6$, 400 MHz) δ6.07 (s, 1H, —S-CH—), 7.10–7.20 (m, 2H, ArH), 7.44 (dd, J=8, 2 Hz, 1H, ArH), 7.70 (d, J=8 Hz, 1H, ArH), 7.81 (d, J=8 Hz, 1H, IR (KBr): 3340 (bd, NH), 1700 (s, C=O), 1632 (m), 1138 (m, doublet), 812 (w) cm$^{-1}$.

MS (EI) m/e (rel. intensity): 291 (M+, 33), 175 (100), 131 (45).

Analysis Calculated: C, 53.59; H, 3.11; N, 4.81. Found: C, 53.45; H, 3.29; N, 4.64.

What is claimed is:

1. A 1- or 2-sulfonylnaphthalene derivative of the formula I

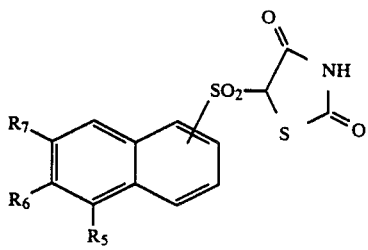

or a pharmaceutically acceptable cationic salt thereof, wherein $R_5$ is hydrogen, bromo, chloro, trifluoromethyl or difluoroethyl;

$R_6$ is hydrogen, hydroxy, methoxy or ethoxy; and $R_7$ is hydrogen or $R_7$ and $R_6$ are both methyl or ethyl carbonate, provided that, when $S(O)_2$ is in the 2 position of the naphthalene ring, $R_5$, $R_6$ and $R_7$ are each hydrogen.

2. A 1-sulfonylnaphthalene derivative of claim 1 in which $R_5$ is hydrogen, bromo or trifluoromethyl.

3. A 1-sulfonylnaphthalene derivative of claim 1 in which $R_5$ is trifluoromethyl and $R_6$ is hydrogen or methoxy.

4. A 1- or 2-sulfonylnaphthalene derivative of claim 1 in which $R_5$, $R_6$ and $R_7$ are each hydrogen.

5. A 1-sulfonylnaphthalene derivative of claim 1 which is 5-[(5-bromo-1-naphthalenyl)sulfonyl]-2,4-thiazolidinedione.

6. A 1-sulfonylnaphthalene derivative of claim 1 which is 5-[(1-naphthalenyl)sulfonyl]-2,4-thiazolidinedione.

7. A 1-sulfonylnaphthalene derivative of claim 1 which is 5-[[(6-methoxy-5-(trifluoromethyl)-1-naphthalenyl]sulfonyl]]-2,4-thiazolidinedione.

8. A 2-sulfonylnaphthalene derivative of claim 1 which is 5-[(2-naphthaleneyl)sulfonyl]-2,4-thiazolidinedione.

* * * * *